United States Patent
Zhou et al.

(10) Patent No.: US 11,713,288 B2
(45) Date of Patent: Aug. 1, 2023

(54) METHOD FOR CO-PRODUCTION OF HYDROFLUOROCARBONS

(71) Applicant: Zhejiang Quhua Fluor-Chemistry Co Ltd, Zhejiang (CN)

(72) Inventors: Iiyang Zhou, Zhejiang (CN); Jiangyong Hong, Zhejiang (CN); Bo Yang, Zhejiang (CN); Yan Zhang, Zhejiang (CN); Bin Wu, Zhejiang (CN); Xinguo Tang, Zhejiang (CN); Huimei Yu, Zhejiang (CN)

(73) Assignee: Zhejiang Quhua Fluor-Chemistry Co Ltd, Zhejiang (CN)

( * ) Notice: Subject to any disclaimer, the term of this patent is extended or adjusted under 35 U.S.C. 154(b) by 73 days.

(21) Appl. No.: 17/627,127

(22) PCT Filed: Jul. 16, 2021

(86) PCT No.: PCT/CN2021/106782
§ 371 (c)(1),
(2) Date: Jan. 14, 2022

(87) PCT Pub. No.: WO2022/042128
PCT Pub. Date: Mar. 3, 2022

(65) Prior Publication Data
US 2022/0371975 A1    Nov. 24, 2022

(30) Foreign Application Priority Data
Aug. 27, 2020  (CN) .......................... 202010874823.2

(51) Int. Cl.
C07C 17/20     (2006.01)
B01J 23/26     (2006.01)
(Continued)

(52) U.S. Cl.
CPC ............. *C07C 17/206* (2013.01); *B01J 23/26* (2013.01); *B01J 23/468* (2013.01); *C07C 17/383* (2013.01)

(58) Field of Classification Search
CPC ..... C07C 17/206; C07C 17/383; C07C 19/08; C07C 17/06; B01J 23/26; B01J 23/468; B01J 21/04; B01J 21/18
See application file for complete search history.

(56) References Cited

U.S. PATENT DOCUMENTS 5,902,913 A    5/1999    Powell et al.

FOREIGN PATENT DOCUMENTS

| CN | 1142220 | 2/1997 |
| CN | 1152905 | 6/1997 |

(Continued)

OTHER PUBLICATIONS

"International Search Report (Form PCT/ISA/210) of PCT/CN2021/106782," dated Sep. 28, 2021, pp. 1-6.
(Continued)

*Primary Examiner* — Jafar F Parsa
(74) *Attorney, Agent, or Firm* — JCIPRNET

(57) ABSTRACT

The present disclosure provides a method for co-production of hydrofluorocarbons, which includes the steps of: preheating a mixture of chlorinated olefin and hydrogen fluoride; transferring the mixture to the top of a reactor; simultaneously introducing 1,1,1,2,3,3-hexafluoropropene and dichloromethane to the middle of the reactor for reaction; dividing the reactor into three to six sections; filling each section with a catalyst; obtaining reaction products at an outlet of the reactor; and separating the reaction products to obtain various hydrofluorocarbon products, respectively. The present disclosure has the advantages of a high yield, an optimal selectivity and a low energy consumption.

10 Claims, 1 Drawing Sheet

(51) Int. Cl.
*B01J 23/46* (2006.01)
*C07C 17/383* (2006.01)

(56) References Cited

FOREIGN PATENT DOCUMENTS

| | | |
|---|---|---|
| CN | 1271337 | 10/2000 |
| CN | 1599704 | 3/2005 |
| CN | 1678551 | 10/2005 |
| CN | 1867530 | 11/2006 |
| CN | 102989496 | 3/2013 |
| CN | 112125777 | 12/2020 |

OTHER PUBLICATIONS

"Written Opinion of the International Searching Authority (Form PCT/ISA/237) of PCT/CN2021/106782," dated Sep. 28, 2021, pp. 1-4.

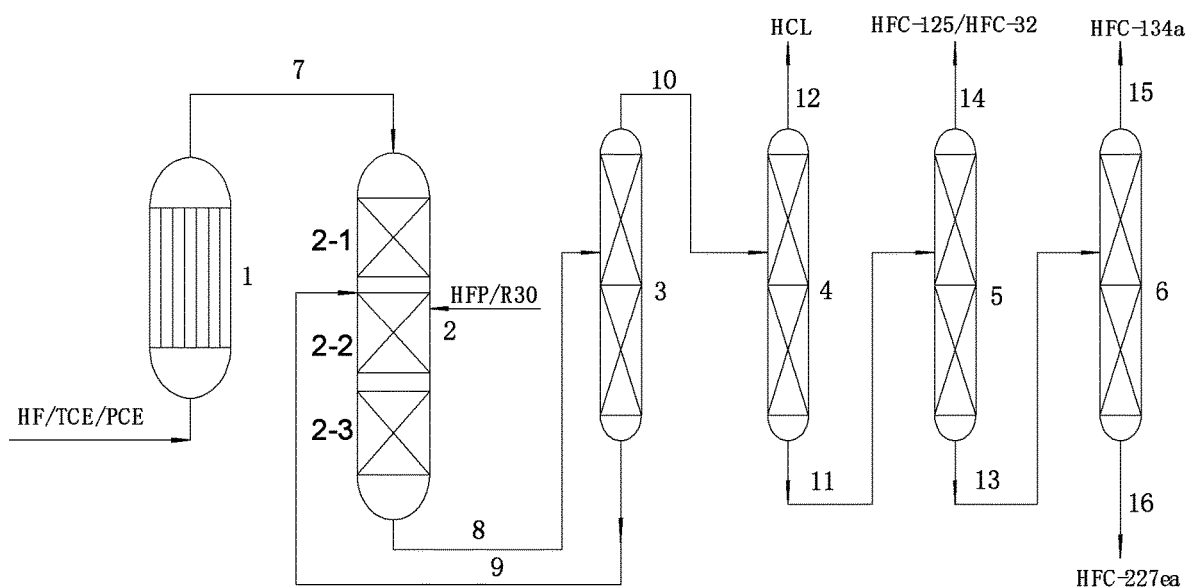

METHOD FOR CO-PRODUCTION OF HYDROFLUOROCARBONS

CROSS-REFERENCE TO RELATED APPLICATION

This application is a 371 of international application of PCT application serial no. PCT/CN2021/106782, filed on Jul. 16, 2021, which claims the priority benefit of China application no. 202010874823.2, filed on Aug. 27, 2020. The entirety of each of the above mentioned patent applications is hereby incorporated by reference herein and made a part of this specification.

TECHNICAL FIELD

The present disclosure relates to a method for production of hydrofluorocarbons (HFCs), in particular to a method for co-production of the HFCs.

RELATED ART

Hydrofluorocarbons (HFCs) are compounds in which some hydrogen atoms in alkanes are replaced with fluorine. These compounds contain no chlorine, causes no damage to the atmospheric ozone layer, and are substitutes for ozone-depleting substances. HFCs include HFC-134a, HFC-125, HFC-32, HFC-245fa, HFC-227ea, etc. The previous ones have been industrialized and mass-produced in mature production lines. 1,1,1,2,3,3,3-heptafluoropropane ($CF_3CHFCF_3$, HFC-227ea for short) is a chlorine-free compound, which is harmless to the atmospheric ozone layer, is widely used as a substitute for halon gas (regarded as an extinguishing agent harmful to the environment) in a gas fire extinguishing system due to its excellent performances, and can also be used as a medium for storing substances sensitive to the atmosphere as well as be used as a propellant for a medical aerosol formulation, or is mixed with ethylene oxide as a disinfectant, etc. A heptafluoropropane fire extinguishing system has been widely used in important places such as urban equipment rooms, substations, transportation and libraries. With the phasing out of chlorofluorocarbons and halons, the industrial importance of the heptafluoropropane as one of the main substitutes for ozone-depleting substances has increased year by year. There are not many disclosed methods for preparing hexafluoropropane, among which a preparation process with an industrial development value adopts addition of anhydrous hydrofluoric acid to hexafluoropropene.

For example, the patent CN 1271337A entitled gas phase preparation of 1,1,1,2,3,3,3-Heptafluoropropane discloses a method for preparing 1,1,1,2,3,3,3-heptafluoropropane by reaction of hydrogen fluoride and hexafluoropropene in a gas phase in the presence of a fluorination catalyst. The reaction can be conducted under an adiabatic condition, which can reduce fouling of the catalyst. A smaller device can be used by using HFC-227ea as a diluent.

For example, the patent CN 1867530A entitles a method for preparation of at least one of 1,1,1,3,3,3-hexafluoropropane and 1,1,1,2,3,3-hexafluoropropane and 1,1,1,2,3,3,3-heptafluoropropane. The method includes the steps of: (a) making HF and $Cl_2$ react with at least one halogenated propylene of a formula $CX_3CCl=CX_2$ (wherein each X independently represents F and Cl) to generate products including $CF_3CCl_2CF_3$ and $CF_3CClFCClF_2$; (b) making the $CF_3CCl_2CF_3$ and the $CF_3CClFCClF_2$ generated in the step (a) react with hydrogen to generate products including $CF_3CH_2CF_3$ and at least one compound selected from $CHF_2CHFCF_3$ and $CF_3CHFCF_3$; and (c) recycling $CF_3CH_2CF_3$ and at least one compound selected from $CHF_2CHFCF_3$ and $CF_3CHFCF_3$. In the step (a), the $CF_3CCl_2CF_3$ and the $CF_3CClFCClF_2$ are generated in the presence of a chlorofluorination catalyst, the chlorofluorination catalyst includes a $ZnCr_2O_4$/crystal Alpha-chromium oxide composition, a $ZnCr_2O_4$/crystal Alpha-chromium oxide composition which has been treated with a fluorinating agent, a zinc halide/Alpha-chromium oxide composition, and/or a zinc halide/Alpha-chromium oxide composition which has been treated with a fluorinating agent. The catalyst is unstable in performance and easy to crystallize.

For example, the patent CN1678551A entitled a method for preparation of 2-chloro-1,1,1,2,3,3,3-heptafluoropropane, hexafluoropropene and 1,1,1,2,3,3,3-heptafluoropropane includes the following steps of: (a) preparing a mixture of hydrogen fluoride, chlorine and at least one raw material selected from halogenated propylene of a formula $CX_3CCl=CX_2$ and halogenated propane of a formula $CX_3CClYCX_3$, where each X is independently selected from F and Cl, and Y is selected from H, Cl and F (provided that the total number of X, Y and F is not larger than 6), and making the mixture have contact with a chlorofluorination catalyst in a reaction area to generate a mixture including $CF_3CClFCF_3$, HCl, HF and a low fluorinated halogenated hydrocarbon intermediate. The method is characterized in that the chlorofluorination catalyst includes at least one chromium-containing component selected from (i) crystal Alpha-chromium oxide, wherein at least 0.05 atomic % of chromium atoms in the Alpha-chromium oxide lattices are substituted both by nickel, trivalent cobalt or divalent nickel ,and trivalent cobalt; and (ii)(i) fluorinated crystalline oxide.

For example, the patent CN 1599704A entitled gas-phase production method for 1,1,1,2,3,3,3-Heptafluoropropane by using hydrogen fluoride and hexafluoropropene, an azeotropic composition of HF and HFC-227ea is used to produce substantially HF-free HFC-227ea, and the unreacted HF is recycled in the reactor. By recycling the azeotropic composition, the HFC-227ea can be used as a diluent, thereby facilitating temperature control of a high exothermic reaction.

For example, the patent CN1152905A entitled method for preparing 1,1,1,2,3,3,3-heptafluoropropane relates to a preparation method for preparing 1,1,1,2,3,3,3-heptafluoropropane by reaction of hexafluoropropane and anhydrous hydrofluoric acid in the presence of an antimony catalyst. The disclosure can provide a preparation method for obtaining HFC-227ea with a high yield under mild conditions without producing by-products such as olefins. The disadvantages are a high product cost, generation of a large amount of by-products, and difficult treatment of spent catalysts.

SUMMARY OF INVENTION

To overcome the shortcomings of the prior art, the present disclosure provides a method for co-production of hydrofluorocarbons, which has a high yield, an optimal selectivity and a low energy consumption.

To solve the above technical problems, the present disclosure adopts a technical solution as follows: A method for co-production hydrofluorocarbons includes the following steps.

(a) A mixture of chlorinated olefin and hydrogen fluoride is preheated and transferred to the top of a reactor, 1,1,1,2, 3,3-hexafluoropropene and dichloromethane are introduced to the middle of the reactor for reaction simultaneously; the reactor is divided into three to six sections; each section is filled with a catalyst; reaction products at an outlet of the reactor are obtained.

(b) The reaction products obtained in the step (a) enters a first rectifying tower for separation to obtain a fraction at the top of the first rectifying tower and a product at the bottom of the first rectifying tower.

(c) The fraction at the top of the first rectifying tower obtained in the step (b) enters a second rectifying tower for separation to obtain hydrogen chloride at the top of the second rectifying tower and a product at the bottom of the second rectifying tower.

(d) The product at the bottom of the second rectifying tower obtained in the step (c) enters a third rectifying tower to obtain a difluoromethane product or a mixture containing difluoromethane at the top of the third rectifying tower and a 1,1,1,2,3,3,3-heptafluoropropane product or a mixture containing 1,1,1,2,3,3,3-heptafluoropropane at the bottom of the third rectifying tower; if there is a mixture containing difluoromethane obtained at the top of the third rectifying tower, conducting further separation to obtain a difluoromethane product; and if there is a mixture containing 1,1,1,2,3,3,3-heptafluoropropane obtained at the bottom of the third rectifying tower, conducting further separation to obtain a 1,1,1,2,3,3,3-heptafluoropropane product.

A general formula of chlorinated olefin in the step (a) of the present disclosure is $C_2Cl_{4-x}Z_x$, wherein x is 0 or 1, and Z is H or Cl.

As a preferred implementation of the present disclosure, the chlorinated olefin in the step (a) is trichloroethylene; the difluoromethane is obtained at the top of the third rectifying tower; a mixture of 1,1,1,2-tetrafluoroethane and the 1,1,1,2,3,3,3-heptafluoropropane is obtained at the bottom of the third rectifying tower and enter a fourth rectifying tower for separation to obtain a 1,1,1,2-tetrafluoroethane product and a 1,1,1,2,3,3,3-heptafluoropropane product, respectively.

As a preferred implementation of the present disclosure, the chlorinated olefin in the step (a) is tetrachloroethylene; a mixture of the difluoromethane and 1,1,1,2,2-pentafluoroethane is obtained at the top of the third rectifying tower; the 1,1,1,2,3,3,3-heptafluoropropane product is obtained at the bottom of the third rectifying tower; and the mixture of the difluoromethane and the 1,1,1,2,2-pentafluoroethane is further separated to obtain a difluoromethane product and a 1,1,1,2,2-pentafluoroethane product, respectively.

As a preferred implementation of the present disclosure, the chlorinated olefin in the step (a) is a mixture of trichloroethylene and tetrachloroethylene; the product at the top of the third rectifying tower is a mixture of the difluoromethane and the 1,1,1,2,2-pentafluoroethane; the product at the bottom of the third rectifying tower is a mixture of the 1,1,1,2-tetrafluoroethane and the 1,1,1,2,3,3,3-heptafluoropropane; the mixture of the difluoromethane and the 1,1,1,2,2-pentafluoroethane is further separated to obtain a difluoromethane product and a 1,1,1,2,2-pentafluoroethane product, respectively; and the mixture of the 1,1,1,2-tetrafluoroethane and the 1,1,1,2,3,3,3-heptafluoropropane enters a fourth rectifying tower to obtain a 1,1,1,2-tetrafluoroethane product and a 1,1,1,2,3,3,3-heptafluoropropane product, respectively.

As a preferred implementation of the present disclosure, a molar ratio of the hydrogen fluoride to the chlorinated olefin in the step (a) is (12-20):1, and a molar ratio of the 1,1,1,2,3,3-hexafluoropropene to the dichloromethane is (1-3):1.

As a preferred implementation of the present disclosure, a pressure of the reaction in the step (a) is 0.8 MPa to 1.2 MPa; a reaction temperature of a first section of the reactor is 200° C. to 250° C.; and a reaction temperature of a second section of the reactor is 280° C. to 350° C.

As a preferred implementation of the present disclosure, the catalyst in the first section of the reactor in the step (a) is chromium (Cr)-loaded aluminum oxide ($Al_2O_3$), wherein the weight percentage content of chromium is 15% to 20%.

As a preferred implementation of the present disclosure, the catalyst in the second section of the reactor in the step (a) is iridium (Ir) and zinc (Zn)-loaded chromium oxide, wherein the weight percentage content of iridium is 10% to 20% and the weight percentage content of zinc is 15% to 30%.

As a preferred implementation of the present disclosure, the catalyst in the third to six sections of the reactor in the step (a) is chromium, magnesium (Mg) and indium (In)-loaded active carbon, wherein the weight percentage content of chromium is 25% to 40%, the weight percentage content of magnesium is 5% to 10%, and the weight percentage content of indium is 3% to 6%.

As a preferred implementation of the present disclosure, the product at the bottom of the first rectifying tower in the step (b) is circulated back into the reactor for further reaction.

According to the present disclosure, a plurality of hydrofluorocarbon (HFCs) products are co-produced by one reactor which can be divided into a plurality of sections, preferably three to six sections, where a raw material mixture of hydrogen fluoride (HF), trichloroethylene (TCE) and/or tetrachloroethylene (PCE) is fed from the top of the reactor; and 1,1,1,2,3,3-hexafluoropropene (HFP) and dichloromethane (R30) are fed sideways to obtain a mixture product containing 1,1,1,2,3,3,3-heptachloropropane (HFC-227ea), 1,1,1,2-tetrafluoroethane (HFC-134a) and/or 1,1,1,2,2-pentafluoroethane (HFC-125) and difluoromethane (HFC-32).

An addition reaction is mainly occurred in a first section of the reactor, which is a strong exothermic reaction, and a catalyst is quickly carbonized. Chromium-loaded aluminum oxide is used as a catalyst in the first section of the present disclosure, chromium loading capacity is 15% to 20% (in percentage by weight), and aluminum oxide carriers can be uniformly distributed with heat. In addition, the present disclosure further reduces the problems of easy deactivation and a short service life of the catalyst at a high temperature by co-production of a plurality of hydrofluorocarbons.

A fluorine and chlorine exchange reaction is mainly occurred in the second section of the reactor, and iridium and zinc-loaded chromium oxide is used as a catalyst, wherein the weight percentage content of iridium is 10% to 20% and the weight percentage content of zinc is 15% to 30%. The addition of iridium can inhibit the generation of $CF_2$=CHCl and $CF_3CF_2Cl$, and improve the selectivity. The addition of zinc can improve the activity of the fluorine and chlorine exchange reaction.

The HFP and R30 raw materials are supplemented sideways in the reactor and react by reaction heat generated in the first section and the second section without external heating. The materials in the second section are directly fed to the third to sixth sections, and a reaction temperature required by the third to sixth sections is provided, thus realizing comprehensive utilization of heat and reducing energy consumption. Chromium, magnesium and indium-loaded active carbon is used as a catalyst in the third to sixth sections, wherein the weight percentage content of chromium is 25% to 40%, the weight percentage content of magnesium is 5% to 10% and the weight percentage content of indium is 3% to 6%. The magnesium is loaded on active carbon to inhibit the carbonization of the catalyst in the strong exothermic reaction between the HFP and the HF. The addition of indium improves the activity of the reaction between the R30 and the HF and reduces the formation of difluorochloromethane (R31).

For a fluorine and chlorine exchange reaction, increasing a concentration of the HF facilitates conversion and generation of products. Meanwhile, the larger the molar ratio of the HF to organic matters, the shorter the induction time of the catalyst, which can prolong the service life of the catalyst. However, a too large molar ratio may cause a large post-treatment load and a high energy consumption.

The conversion and selectivity of raw materials decrease with the increase of a space velocity. With a larger space velocity, organic materials passing through the catalyst surface in unit time will be increased, which causes easy carbon deposition and affects the service life of the catalyst. With a smaller space velocity, carbon deposition can be reduced, but a space time yield of the catalyst at the moment will be lowered.

By increasing a pressure, a contact time between the reaction materials and the catalyst can be prolonged, which facilitates improvement of the conversion and selectivity, and accelerates the generation velocity of HFC-134a/HFC-125 and HFC-32.

Based on overall consideration of the above factors, a molar ratio of the hydrogen fluoride to the chlorinated olefin is controlled to be (12-20):1, a molar ratio of the 1,1,1,2,3, 3-hexafluoropropylene to the dichloromethane is controlled to be (1-3):1, a reaction pressure is controlled to be 0.8 MPa to 1.2 MPa, and a reaction temperature is controlled to be 200° C. to 250° C.

The reactor of the present disclosure is divided into a plurality of sections, and heat between the sections can be removed by heat exchange tubes, which achieves a high efficiency and saves energy. All the sections can be correspondingly filled with catalysts with different functions according to different reaction properties, which are suitable for co-production of HFCs products. The reactor in the present disclosure can be isothermal or adiabatic, and the reactor can be selected from an acid-resistant material such as Inconel. Perforated baffles can be arranged among the sections of the reactor; the catalysts are loaded from bottom to top according to the sequence from the sixth section to the first section; and the catalysts are preferably spherical or columnar, which keeps a smooth reaction gas velocity, ensures a uniform void ratio and prevents a gas mixture from being dispersed in the axial direction and the radial direction.

The catalysts used in all the sections of the reactor of the present disclosure can be prepared by methods known in the art. For example, the catalyst used in the first section can be prepared by a method including the following steps.

Aluminum oxide with a diameter of 4 mm is dried at 150° C. for 10 hours and calcined at 380° C. for 5 h; $CrCl_3.6H_2O$ or $Cr(NO_3)_3.6H_2O$ is weighed to prepare a chromium salt solution; the treated aluminum oxide is impregnated for 24 h, dried at 150° C. for 5 h, and calcined at 350° C. for 3 h to obtain a required catalyst. The prepared catalyst is charged to a reactor and heated to 350° C., dried with nitrogen for 6 h, and cooled to 300° C.; anhydrous hydrogen fluoride diluted with nitrogen is introduced, and conducted an activation treatment for 48 h under a condition that a hot spot of a catalyst bed is controlled not to exceed 350° C. to obtain an activated catalyst.

The catalyst in the second section can be prepared by a method including the following steps.

Chromium chloride, iridium chloride and zinc chloride are prepared according to a certain proportion, and urea with a concentration of 20% is added as a precipitant; after a precipitation reaction, it is filtered, washed, dried at 120° C. for 24 h, roasted at 340° C. for 10 h in a nitrogen environment, and pressing a product into columnar particles with a diameter of 3 mm and a height of 3 mm to obtain a required catalyst. The prepared catalyst is charged to a reactor and heated to 320° C.; anhydrous hydrogen fluoride diluted with nitrogen is introduced, and conducted an activation treatment for 48 h under a condition that a hot spot of a catalyst bed is controlled not to exceed 350° C. to obtain an activated catalyst.

The catalysts used in the third to sixth sections can be prepared by a method including the following steps of: soaking active carbon with a diameter of 1.5 mm and a length of 3-4 mm with 5% nitric acid for 3 h; drying at 120° C. for 5 h; soaking in a chromium chloride, magnesium chloride and indium nitrate solution according to a proportion; and roasting at 400° C. for 15 h in a nitrogen environment to obtain required catalysts; charging the prepared catalysts to a reactor and heating to 350° C. in; introducing anhydrous hydrogen fluoride diluted with nitrogen; and conducting an activation treatment for 30 h under a condition that a hot spot of a catalyst bed is controlled not to exceed 400° C. to obtain activated catalysts.

Compared with the prior art, the present disclosure has the following advantages.

(1) The process is simple; the reactor is filled with three different catalysts to conduct three reactions, so the process flow is simplified. By one set of device, a plurality of hydrofluorocarbon products can be co-produced at the same time. The proportion of each hydrofluorocarbon product can be controlled by changing the reaction conditions, thus realizing intensive production.

(2) A conversion rate of TCE/PCE and HFP is as high as 100% due to adjustment parameters such as a molar ratio and optimization of the catalysts, the reaction temperature and the space velocity, etc.

(3) A lower energy consumption is achieved. Excluding the reactors in the first section and the second section, the reactors in the other sections do not need to be heated externally; the materials of the second section are directly fed to the third to sixth sections in sequence and a required reaction temperature is provided, thus realizing comprehensive utilization of heat and remarkably reducing energy consumption.

(4) Small investment and large operation flexibility are achieved. The reactor is sectioned in design. The catalysts are loaded according to functions flexibly and variably, so that a plurality of HFCs products can be co-produced in one reactor at the same time. The proportion of the products can be flexibly adjusted according to markets, and equipment investment is remarkably reduced.

BRIEF DESCRIPTION OF DRAWINGS

FIGURE is a process flow diagram of Example 1 of the present disclosure.

As shown in the figures: 1 is a preheater, 2 is a reactor, 3 is a first rectifying tower, 4 is a second rectifying tower, 5 is a third rectifying tower, 6 is a fourth rectifying tower, 7-16 are pipelines, 2-1 is the first section of the reactor, 2-2 is the second section of the reactor, and 2-3 is the third section of the reactor.

DESCRIPTION OF EMBODIMENTS

A process flow of the present disclosure is shown in FIG. 1. Taking a three-section reactor as an example, the reactor 2 is divided into three sections; the first section 2-1, the second section 2-2 and the third section 2-3 of the reactor are each filled with a catalyst; fresh HF, TCE and/or PCE are preheated by a preheater 1 and enter the first section 2-1 of the reactor through a pipeline 7 to react; reaction products, together with sideway-fed HFP and R30, enter the second section 2-2 of the reactor to react; products obtained in the second section 2-2 of the reactor enter the third section 2-3 of the reactor to react; a mixture obtained in the third section 2-3 of the reactor enters a first rectifying tower 3 through a pipeline 8 to be separated; heavy components containing unreacted 1,1,1-trifluoro-2-chloroethane (HCFC-133a) and/or 2,2-dichloro-1,1,1-trifluoroethane (HCFC-123), 2-dichloro-1,1,1,2-tetrafluoroethane (HCFC-124), difluorochloromethane (R31), HF and the like at the bottom of the first rectifying tower 3 are returned to the second section of the reactor 2 through a pipeline 9 to react; light components containing HFC-134a and/or HFC-125, HFC-227ea, HFC-32 and HCl at the top enter a second rectifying tower 4 through a pipeline 10; HCl is separated from the top of the second rectifying tower 4 through a pipeline 12 and is further refined to obtain hydrochloric acid; a mixture containing HFC-134a and/or HFC-125, HFC-227ea and HFC-32 at the bottom enters a third rectifying tower 5 through a pipeline 11; an HFC-32 product or a mixture of HFC-32 and HFC-125 is obtained from the top of the third rectifying tower 5 through a pipeline 14; when there is a mixture of the HFC-32 and the HFC-125 obtained at the top of the third rectifying tower, the mixture is subjected to further general separation such as rectification in the art to obtain the HFC-32 product and the HFC-125 product, respectively; there is the HFC-227ea product or the mixture of the HFC-227ea and the HFC-134a obtained at the bottom of the third rectifying tower 5; when there is the mixture of the HFC-227ea and the HFC-134a obtained at the bottom of the third rectifying tower 5, the mixture of the HFC-227ea and the HFC-134a is further separated in a fourth rectifying tower 6 through a pipeline 13; the HFC-134a product is obtained from the top of the fourth rectifying tower 6 through a pipeline 15; and the HFC-227ea product is obtained from the bottom through a pipeline 16.

The present disclosure is further described in detail below in conjunction with examples, but is not limited by the following examples.

EXAMPLE 1

The reactor was divided into three sections; first, 100 ml of an activated (Cr-Mg-In)/C catalyst (with 30% of Cr, 10% of Mg and 5% of In in percentage by weight) was loaded in the third section of the reactor; 100 ml of an activated (Ir-Zn)/chromium oxide catalyst (with 10% of Ir and 20% of Zn in percentage by weight) was loaded in the second section of the reactor; and 100 ml of an activated $Cr/Al_2O_3$ catalyst (with 15% of Cr in percentage by weight) was loaded in the first section of the reactor.

A temperature of the reactor was adjusted to a reaction temperature; materials were fed for reaction; HF, TCE and PCE were mixed and preheated, and reacted in the reactor; meanwhile, 1,1,1,2,3,3-hexafluoropropene and dichloromethane reacted in the middle of the reactor; a molar ratio of hydrogen fluoride to the total moles of TCE and PCE was 12:1; a molar ratio of TCE to PCE was 1:1; a molar ratio of the 1,1,1,2,3,3-hexafluoropropene to the dichloromethane was 2:1; a pressure of the reaction is 0.9 MPa; the reaction temperature in the first section of the reactor is 200° C.; and the reaction temperature in the second section of the reactor is 290° C. A mixture at an outlet of the reactor was sampled and subjected to gas chromatographic analysis, and results are shown in Table 1.

EXAMPLE 2

The reactor was divided into three sections; first, 100 ml of an activated (Cr-Mg-In)/C catalyst (with 30% of Cr, 5% of Mg and 5% of In in percentage by weight) was loaded in the third section of the reactor; 100 ml of an activated (Ir-Zn)/chromium oxide catalyst (with 15% of Ir and 25% of Zn in percentage by weight) was loaded in the second section of the reactor; and 100 ml of an activated $Cr/Al_2O_3$ catalyst (with 15% of Cr in percentage by weight) was loaded in the first section of the reactor.

A temperature of the reactor was adjusted to a reaction temperature; materials were fed for reaction; HF, TCE and PCE were mixed and preheated, and reacted in the reactor; meanwhile, 1,1,1,2,3,3-hexafluoropropene and dichloromethane reacted in the middle of the reactor; a molar ratio of hydrogen fluoride to the total moles of TCE and PCE was 15:1; a molar ratio of TCE to PCE was 0.5:1; a molar ratio of the 1,1,1,2,3,3-hexafluoropropene to the dichloromethane was 1:1; a pressure of the reaction is 0.8 MPa; the reaction temperature in the first section of the reactor is 230° C.; and the reaction temperature in the second section of the reactor was conducted at 310° C. A mixture at an outlet of the reactor was sampled and subjected to gas chromatographic analysis, and results are shown in Table 1.

EXAMPLE 3

The reactor was divided into three sections; first, 100 ml of an activated (Cr—Mg—In)/C catalyst (with 25% of Cr, 5% of Mg and 3% of In in percentage by weight) was loaded in the third section of the reactor; 100 ml of an activated (Ir—Zn)/chromium oxide catalyst (with 10% of Ir and 15% of Zn in percentage by weight) was loaded in the second section of the reactor; and 100 ml of an activated $Cr/Al_2O_3$ catalyst (with 15% of Cr in percentage by weight) was loaded in the first section of the reactor.

A temperature of the reactor was adjusted to a reaction temperature; materials were fed for reaction; HF, TCE and PCE were mixed and preheated, and reacted in the reactor; meanwhile, 1,1,1,2,3,3-hexafluoropropene and dichloromethane reacted in the middle of the reactor; a molar ratio of hydrogen fluoride to the total moles of TCE and PCE was 15:1; a molar ratio of TCE to PCE was 2:1; a molar ratio of the 1,1,1,2,3,3-hexafluoropropene to the dichloromethane was 3:1; a pressure of the reaction is 1.0 MPa; the reaction temperature in the first section of the reactor is 250° C.; and the reaction temperature in the second section of the reactor is 300° C. A mixture at an outlet of the reactor was sampled and subjected to gas chromatographic analysis, and results are shown in Table 1.

EXAMPLE 4

The reactor was divided into four sections; first, 100 ml of an activated (Cr—Mg—In)/C catalyst (with 35% of Cr, 10% of Mg and 5% of In in percentage by weight) was loaded in the fourth section of the reactor; 100 ml of the activated (Cr—Mg—In)/C catalyst (with 35% of Cr, 10% of Mg and 5% of In in percentage by weight) was loaded in the third section of the reactor; 100 ml of an activated (Ir—Zn)/ chromium oxide catalyst (with 18% of Ir and 30% of Zn in percentage by weight) was loaded in the second section of the reactor; and 100 ml of an activated $Cr/Al_2O_3$ catalyst (with 17% of Cr in percentage by weight) was loaded in the first section of the reactor finally.

A temperature of the reactor was adjusted to a reaction temperature; materials were fed for reaction; HF, TCE and PCE were mixed and preheated, and reacted in the reactor; meanwhile, 1,1,1,2,3,3-hexafluoropropene and dichloromethane reacted in the middle of the reactor; a molar ratio of hydrogen fluoride to the total moles of TCE and PCE was 18:1; a molar ratio of TCE to PCE was 1:2; a molar ratio of the 1,1,1,2,3,3-hexafluoropropene to the dichloromethane was 1:1; a pressure of the reaction is 1.2 MPa; the reaction temperature in the first section of the reactor is 240° C.; and the reaction temperature in the second section of the reactor is 330° C. A mixture at an outlet of the reactor was sampled and subjected to gas chromatographic analysis, and results are shown in Table 1.

EXAMPLE 5

The reactor was divided into four sections; first, 100 ml of an activated (Cr—Mg—In)/C catalyst (with 35% of Cr, 10% of Mg and 6% of In in percentage by weight) was loaded in the fourth section of the reactor; 100 ml of the activated (Cr—Mg—In)/C catalyst (with 35% of Cr, 10% of Mg and 6% of In in percentage by weight) was loaded in the third section of the reactor; 100 ml of an activated (Ir—Zn)/ chromium oxide catalyst (with 15% of Ir and 15% of Zn in percentage by weight) was loaded in the second section of the reactor; and 100 ml of an activated $Cr/Al_2O_3$ catalyst (with 17% of Cr in percentage by weight) was loaded in the first section of the reactor.

A temperature of the reactor was adjusted to a reaction temperature; materials were fed for reaction; HF, TCE and PCE were mixed and preheated, and reacted in the reactor; meanwhile, 1,1,1,2,3,3-hexafluoropropene and dichloromethane reacted in the middle of the reactor; a molar ratio of hydrogen fluoride to the total moles of TCE and PCE was 18:1; a molar ratio of TCE to PCE was 3:1; a molar ratio of the 1,1,1,2,3,3-hexafluoropropene to the dichloromethane was 2:1; a pressure of the reaction is 1.1 MPa; the reaction temperature in the first section of the reactor is 230° C.; and the reaction temperature in the second section of the reactor is 340° C. A mixture at an outlet of the reactor was sampled and subjected to gas chromatographic analysis, and results are shown in Table 1.

EXAMPLE 6

The reactor was divided into four sections; first, 100 ml of an activated (Cr—Mg—In)/C catalyst (with 40% of Cr, 10% of Mg and 5% of In in percentage by weight) was loaded in the fourth section of the reactor; 100 ml of the activated (Cr—Mg—In)/C catalyst (with 40% of Cr, 10% of Mg and 5% of In in percentage by weight) was loaded in the third section of the reactor; 100 ml of an activated (Ir—Zn)/ chromium oxide catalyst (with 20% of Ir and 15% of Zn in percentage by weight) was loaded in the second section of the reactor; and 100 ml of an activated $Cr/Al_2O_3$ catalyst (with 17% of Cr in percentage by weight) was loaded in the first section of the reactor.

A temperature of the reactor was adjusted to a reaction temperature; materials were fed for reaction; HF, TCE and PCE were mixed and preheated, and reacted in the reactor; meanwhile, 1,1,1,2,3,3-hexafluoropropene and dichloromethane reacted in the middle of the reactor; a molar ratio of hydrogen fluoride to the total moles of TCE and PCE was 20:1; a molar ratio of TCE to PCE was 4:1; a molar ratio of the 1,1,1,2,3,3-hexafluoropropene to the dichloromethane was 3:1; a pressure of the reaction is 1.0 MPa; the reaction temperature in the first section of the reactor is 220° C.; and the reaction temperature in the second section of the reactor is 350° C. A mixture at an outlet of the reactor was sampled and subjected to gas chromatographic analysis, and results are shown in Table 1.

EXAMPLE 7

The reactor was divided into five sections; first, 100 ml of an activated (Cr—Mg—In)/C catalyst (with 40% of Cr, 5% of Mg and 3% of In in percentage by weight) was loaded in each of the fifth section, the fourth section and the third section of the reactor; 100 ml of an activated (Ir—Zn)/ chromium oxide catalyst (with 20% of Ir and 20% of Zn in percentage by weight) was loaded in the second section of the reactor; and 100 ml of an activated $Cr/Al_2O_3$ catalyst (with 17% of Cr in percentage by weight) was loaded in the first section of the reactor finally.

A temperature of the reactor was adjusted to a reaction temperature; materials were fed for reaction; HF and TCE were mixed and preheated, and reacted in the reactor; meanwhile, 1,1,1,2,3,3-hexafluoropropene and dichloromethane reacted in the middle of the reactor; a molar ratio of the HF to the TCE was 13:1; a molar ratio of the 1,1,1,2,3,3-hexafluoropropene to the dichloromethane was 2:1; a pressure of the reaction is 1.2 MPa; the reaction temperature in the first section of the reactor is 240° C.; and the reaction temperature in the second section of the reactor is 320° C. A mixture at an outlet of the reactor was sampled and subjected to gas chromatographic analysis, and results are shown in Table 1.

EXAMPLE 8

The reactor was divided into five sections; first, 100 ml of an activated (Cr—Mg—In)/C catalyst (with 30% of Cr, 8% of Mg and 4% of In in percentage by weight) was loaded in each of the fifth section, the fourth section and the third section of the reactor; 100 ml of an activated (Ir—Zn)/ chromium oxide catalyst (with 20% of Ir and 30% of Zn in percentage by weight) was loaded in the second section of the reactor; and 100 ml of an activated $Cr/Al_2O_3$ catalyst (with 20% of Cr in percentage by weight) was loaded in the first section of the reactor finally.

A temperature of the reactor was adjusted to a reaction temperature; materials were fed for reaction; HF and TCE were mixed and preheated, and reacted in the reactor; meanwhile, 1,1,1,2,3,3-hexafluoropropene and dichloromethane reacted in the middle of the reactor; a molar ratio of the HF to the TCE was 15:1; a molar ratio of the 1,1,1,2,3,3-hexafluoropropene to the dichloromethane was 1:1; a pressure of the reaction is 0.8 MPa; the reaction temperature in the first section of the reactor is 210° C.; and the reaction temperature in the second section of the reactor is 310° C. A mixture at an outlet of the reactor was sampled and subjected to gas chromatographic analysis, and results are shown in Table 1.

EXAMPLE 9

The reactor was divided into six sections; first, 100 ml of an activated (Cr—Mg—In)/C catalyst (with 25% of Cr, 8% of Mg and 6% of In in percentage by weight) was loaded in each of the fifth section, the fourth section and the third section of the reactor; 100 ml of an activated (Ir—Zn)/chromium oxide catalyst (with 15% of Ir and 20% of Zn in percentage by weight) was loaded in the second section of the reactor; and 100 ml of an activated Cr/Al$_2$O$_3$ catalyst (with 20% of Cr in percentage by weight) was loaded in the first section of the reactor finally.

A temperature of the reactor was adjusted to a reaction temperature; materials were fed for reaction; HF and PCE were mixed and preheated, and reacted in the reactor; meanwhile, 1,1,1,2,3,3-hexafluoropropene and dichloromethane reacted in the middle of the reactor; a molar ratio of the HF to the PCE was 13:1; a molar ratio of the 1,1,1,2,3,3-hexafluoropropene to the dichloromethane was 3:1; a pressure of the reaction is 1.0 MPa; the reaction temperature in the first section of the reactor is 210° C.; and the reaction temperature in the second section of the reactor is 320° C. A mixture at an outlet of the reactor was sampled and subjected to gas chromatographic analysis, and results are shown in Table 1.

EXAMPLE 10

The reactor was divided into six sections; first, 100 ml of an activated (Cr—Mg—In)/C catalyst (with 30% of Cr, 10% of Mg and 3% of In in percentage by weight) was loaded in each of the sixth section, the fifth section, the fourth section and the third section of the reactor; 100 ml of an activated (Ir—Zn)/chromium oxide catalyst (with 10% of Ir and 30% of Zn in percentage by weight) was loaded in the second section of the reactor; and 100 ml of an activated Cr/Al$_2$O$_3$ catalyst (with 20% of Cr in percentage by weight) was loaded in the first stage of the reactor.

A temperature of the reactor was adjusted to a reaction temperature; materials were fed for reaction; HF and PCE were mixed and preheated, and reacted in the reactor; meanwhile, 1,1,1,2,3,3-hexafluoropropene and dichloromethane reacted in the middle of the reactor; a molar ratio of the HF to the PCE was 18:1; a molar ratio of the 1,1,1,2,3,3-hexafluoropropene to the dichloromethane was 2:1; a pressure of the reaction is 1.2 MPa; the reaction temperature in the first section of the reactor is 230° C.; and the reaction temperature in the second section of the reactor is 320° C. A mixture at an outlet of the reactor was sampled and subjected to gas chromatographic analysis, and results are shown in Table 1.

TABLE 1

Test results of Examples 1-10

| Examples | TCE/PCE Conversion Rate (%) | HFP Conversion Rate (%) | R30 Conversion Rate (%) | Overall Selectivity (%) of HFCs |
|---|---|---|---|---|
| 1 | 100 | 100 | 98.5 | 99.7 |
| 2 | 100 | 100 | 99 | 99.8 |
| 3 | 100 | 100 | 99.1 | 99.9 |
| 4 | 100 | 100 | 98.9 | 99.4 |
| 5 | 100 | 100 | 99.2 | 99.5 |
| 6 | 100 | 100 | 98.4 | 99.2 |
| 7 | 100 (TCE) | 100 | 99.3 | 99.9 |
| 8 | 100 (TCE) | 100 | 98.6 | 99.8 |
| 9 | 100 (PCE) | 100 | 98.4 | 99.7 |
| 10 | 100 (PCE) | 100 | 98.7 | 99.5 |

What is claimed is:

1. A method for co-production of hydrofluorocarbons, comprising the following steps of:
   (a) preheating a mixture of chlorinated olefin and hydrogen fluoride; transferring the mixture to the top of a reactor; simultaneously introducing 1,1,1,2,3,3-hexafluoropropene and dichloromethane to the middle of the reactor for reaction; dividing the reactor into three to six sections; filling each section with a catalyst; obtaining reaction products at an outlet of the reactor;
   (b) separating the reaction products obtained in the step (a) in a first rectifying tower to obtain a fraction at the top of the first rectifying tower and a product at the bottom of the first rectifying tower;
   (c) separating the fraction at the top of the first rectifying tower obtained in the step (b) in a second rectifying tower to obtain hydrogen chloride at the top of the second rectifying tower and a product at the bottom of the second rectifying tower; and
   (d) separating the product at the bottom of the second rectifying tower obtained in the step (c) in a third rectifying tower to obtain a difluoromethane product or a mixture containing difluoromethane at the top of the third rectifying tower as well as a 1,1,1,2,3,3,3-heptafluoropropane product or a mixture containing 1,1,1,2,3,3,3-heptafluoropropane at the bottom of the third rectifying tower; if there is a mixture containing difluoromethane obtained at the top of the third rectifying tower, conducting further separation to obtain a difluoromethane product; and if there is a mixture containing 1,1,1,2,3,3,3-heptafluoropropane obtained at the bottom of the third rectifying tower, conducting further separation to obtain a 1,1,1,2,3,3,3-heptafluoropropane product.

2. The method for co-production of hydrofluorocarbons according to claim 1, wherein the chlorinated olefin in the step (a) is trichloroethylene; the difluoromethane is obtained at the top of the third rectifying tower; a mixture of 1,1,1,2-tetrafluoroethane and the 1,1,1,2,3,3,3-heptafluoropropane is obtained at the bottom of the third rectifying tower and is separated in a fourth rectifying tower to obtain a 1,1,1,2-tetrafluoroethane product and a 1,1,1,2,3,3,3-heptafluoropropane product, respectively.

3. The method for co-production of hydrofluorocarbons according to claim 1, wherein the chlorinated olefin in the step (a) is tetrachloroethylene; a mixture of the difluoromethane and 1,1,1,2,2-pentafluoroethane is obtained at the top of the third rectifying tower; the 1,1,1,2,3,3,3-heptafluoropropane product is obtained at the bottom of the third rectifying tower; and the mixture of the difluoromethane and the 1,1,1,2,2-pentafluoroethane is further separated to obtain a difluoromethane product and a 1,1,1,2,2-pentafluoroethane product, respectively.

4. The method for co-production of hydrofluorocarbons according to claim 1, wherein the chlorinated olefin in the step (a) is a mixture of trichloroethylene and tetrachloroethylene; the product at the top of the third rectifying tower is a mixture of the difluoromethane and the 1,1,1,2,2-pentafluoroethane;

the product at the bottom of the third rectifying tower is a mixture of the 1,1,1,2-tetrafluoroethane and the 1,1,1,2,3,3,3-heptafluoropropane; the mixture of the difluoromethane and the 1,1,1,2,2-pentafluoroethane is further separated to obtain a difluoromethane product and a 1,1,1,2,2-pentafluoroethane product, respectively; and the mixture of the 1,1,1,2-tetrafluoroethane and the 1,1,1,2,3,3,3-heptafluoropropane is separated in a fourth rectifying tower to obtain a 1,1,1,2-tetrafluoroethane product and a 1,1,1,2,3,3,3-heptafluoropropane product, respectively.

5. The method for co-production of hydrofluorocarbons according to claim 1, wherein a molar ratio of the hydrogen fluoride to the chlorinated olefin in the step (a) is (12-20):1, and a molar ratio of the 1,1,1,2,3,3-hexafluoropropene to the dichloromethane is (1-3):1.

6. The method for co-production of hydrofluorocarbons according to claim 1, wherein the reaction in the step (a) is performed at a pressure of 0.8 MPa to 1.2 MPa; in a first section of the reactor, the reaction temperature is 200° C. to 250° C.; and at a second section of the reactor, the reaction temperature is 280° C. to 350° C. .

7. The method for co-production of hydrofluorocarbons according to claim 1, wherein the catalyst in the first section of the reactor in the step (a) is chromium-loaded aluminum oxide, wherein the weight percentage content of chromium is 15% to 20%.

8. The method for co-production of hydrofluorocarbons according to claim 1, wherein the catalyst in the second section of the reactor in the step (a) is iridium and zinc-loaded chromium oxide, wherein the weight percentage content of iridium is 10% to 20% and the weight percentage content of zinc is 15% to 30%.

9. The method for co-producing hydrofluorocarbons according to claim 1, wherein the catalyst in the third to six sections of the reactor in the step (a) is chromium, magnesium and indium-loaded active carbon, wherein the weight percentage content of chromium is 25% to 40%, the weight percentage content of magnesium is 5% to 10% and the weight percentage content of indium is 3% to 6%.

10. The method for co-production of hydrofluorocarbons according to claim 1, wherein the product at the bottom of the first rectifying tower in the step (b) is circulated back into the reactor for further reaction.

\* \* \* \* \*

UNITED STATES PATENT AND TRADEMARK OFFICE
CERTIFICATE OF CORRECTION

PATENT NO. : 11,713,288 B2
APPLICATION NO. : 17/627127
DATED : August 1, 2023
INVENTOR(S) : liyang Zhou et al.

Page 1 of 1

It is certified that error appears in the above-identified patent and that said Letters Patent is hereby corrected as shown below:

On the Title Page

Item (72) Inventors should read: liyang ZHOU, Zhejiang (CN); Jiangyong HONG, Zhejiang (CN); Bo YANG, Zhejiang (CN); Yan ZHANG, Zhejiang (CN); Bin WU, Zhejiang (CN); Xinguo TANG, Zhejiang (CN); Huimei YU, Zhejiang (CN)

Signed and Sealed this
Twelfth Day of September, 2023

Katherine Kelly Vidal
*Director of the United States Patent and Trademark Office*